US00PP14765P2

(12) United States Plant Patent
Fear et al.

(10) Patent No.: US PP14,765 P2
(45) Date of Patent: May 4, 2004

(54) BLACKBERRY PLANT NAMED 'DRISCOLL EUREKA'

(50) Latin Name: *Rubus L. subgenus Rubus*
Varietal Denomination: Driscoll Eureka

(75) Inventors: Carlos D. Fear, Aptos, CA (US); Gavin Sills, Watsonville, CA (US); Fred M. Cook, Aptos, CA (US); Richard E. Harrison, Aptos, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 10/306,455

(22) Filed: Nov. 27, 2002

(51) Int. Cl.[7] ..... A01H 5/00
(52) U.S. Cl. ..... Plt./203
(58) Field of Search ..... Plt./203

(56) References Cited

PUBLICATIONS

The Newsletter of The North American Bramble Growers Association, Inc., "The Past, Present and Future of the American Black Raspberry," vol. 18, Issue 1, Spring 2002.*

* cited by examiner

*Primary Examiner*—Anne Marie Grunberg
*Assistant Examiner*—Susan McCormick-Ewoldt
(74) *Attorney, Agent, or Firm*—Pennie & Edmonds LLP

(57) ABSTRACT

The present invention relates to a new and distinct cultivar of blackberry plant named Driscoll Eureka. The new cultivar is distinguished from other blackberry cultivars by its early season, low chill requirement and improved quality and shipping characteristics. The new cultivar is distinguished from its seed parent by being early and having better flavored fruit, it is distinguished from its pollen parent by its better flavor.

2 Drawing Sheets

Latin name of the genus and species of the plant claimed: The variety is botanically identified as *Rubus L.* subgenus *Rubus*.

BACKGROUND OF THE INVENTION

This invention relates to a new cultivar of blackberry called 'Driscoll Eureka' . The new cultivar was developed from hybridization of the female cultivar 'Zorro' (U.S. patent application Ser. No. 09/772,327) with the unpatented male selection BY45.1. The parents were crossed in 1996 where after fruit and seed were collected to produce seedlings for field planting in Watsonville, Calif. in 1997. The new cultivar was selected in 1998 for its good flavor and fruit firmness. The cultivar has been asexually propagated in Watsonville, Calif. and reproduced true to type plants by in vitro shoot tip culture.

SUMMARY OF THE INVENTION

The present invention provides a new and distinct blackberry cultivar named 'Driscoll Eureka'. The variety is botanically identified as *Rubus L.* subgenus *Rubus*. The variety is a complex Rubus hybrid, which can be characterized as an erect tetraploid with considerable *R. alleghenienses* background with other species such as *R. trivialis, R. argutus, R. procerus*, and *R. ulmifolious* also appearing in its background. The new cultivar produces a floricane crop which begins in May and continues until late July. The new blackberry variety is distinguished from other varieties by a number of characteristics as set forth in Table 1. In particular, the new cultivar is distinguished by its early season, its low chill requirement, and its improved quality and shipping characteristics.

COMPARISON TO SIMILAR VARIETIES

The variety that we believe to be similar to 'Driscoll Eureka' from those known to us is 'Olallie', an unpatented variety. 'Driscoll Eureka' is particularly different from 'Olallie' by being slightly earlier ripening, having less postharvest color reversion, having less acidic flavor, and having better fruit firmness. Further detailed comparison of 'Driscoll Eureka' to 'Olallie' and 'Chester' is presented in Table 1.

BRIEF DESCRIPTION OF THE DRAWINGS

The accompanying photographs show typical specimens of the fruit, leaves and shoot of the new cultivar, in color as nearly true as reasonably possible in color illustrations of this type.

DESCRIPTION OF THE NEW VARIETY

Figure 1:
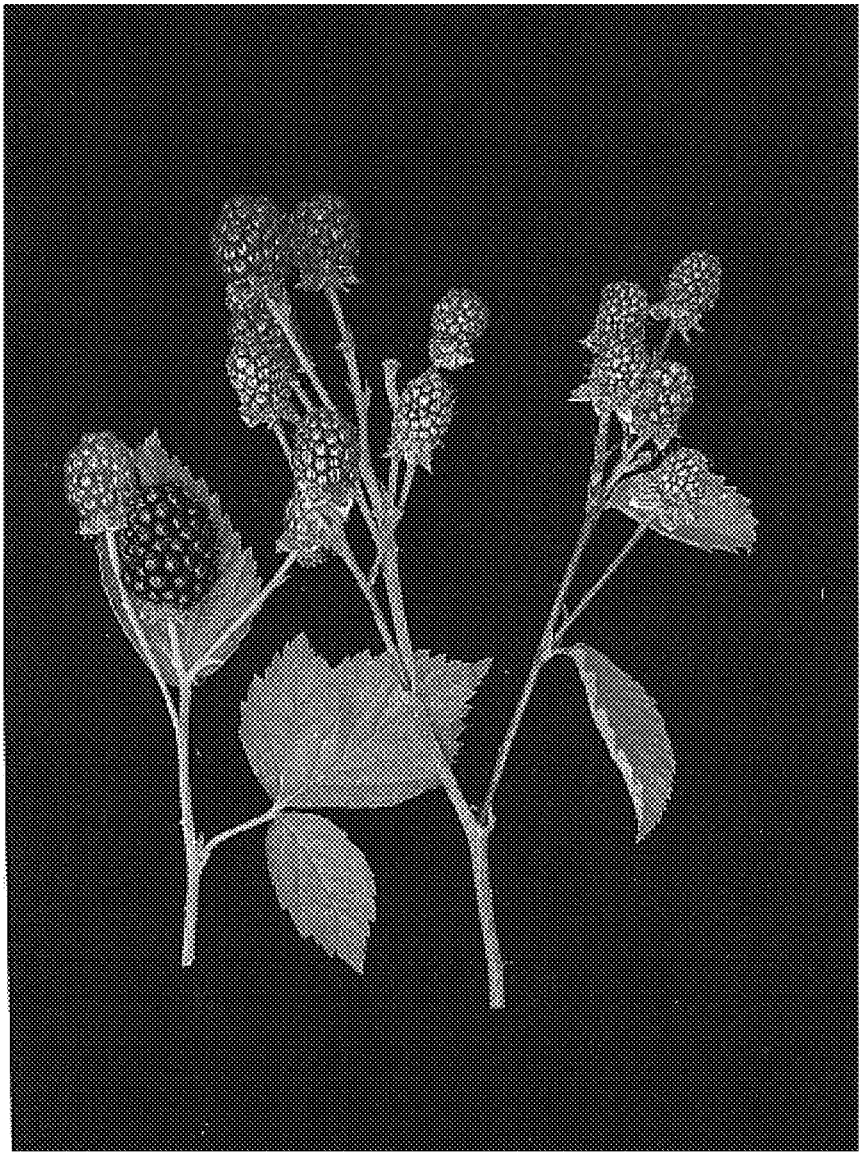
FIG. 1. is a photograph of a 'Driscoll Eureka' fruiting lateral with fruit in various stages of development.
Figure 2:
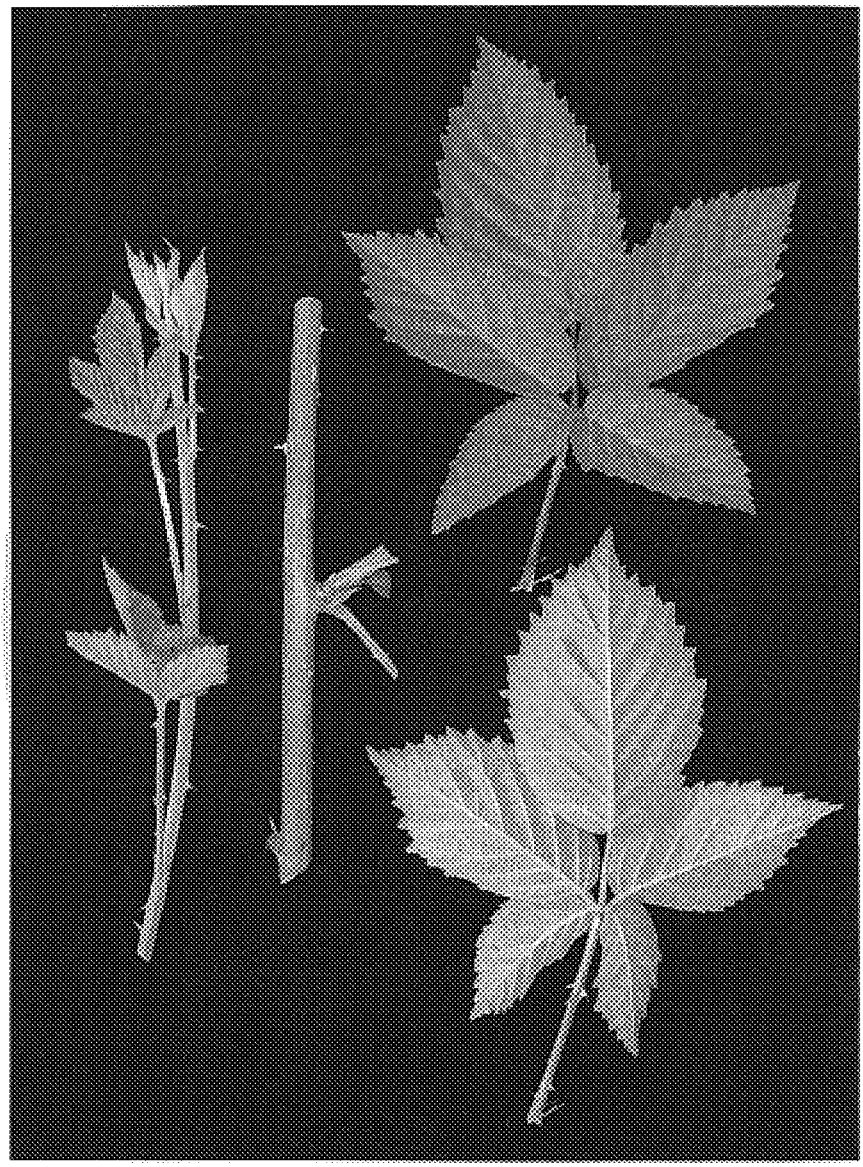
FIG. 2. is a photograph showing a close-up view of a primocane shoot, mature leaf and stem of 'Driscoll Eureka'.

The following detailed description of the new blackberry cultivar, 'Driscoll Eureka', is based upon recorded observations of 2 to 5 year old plants and fruit grown between 2000 and 2002 in Watsonville, Calif. and is believed to apply to plants of the 'Driscoll Eureka' cultivar grown in similar conditions of soil and climate elsewhere. Plants were planted in soil previously pre-plant fumigated and regularly fertilized and irrigated with drip irrigation. This description is in accordance with terminology used by the International Union for the Protection of New Varieties of Plants (UPOV). Throughout this specification, color names beginning with a small letter signify that the name of the color, as used in common speech, is aptly descriptive. Color data with a capital letter and an alphanumeric code indicate the most similar color designations as provided by The Royal Horticultural Society (R.H.S.) Colour Chart published by The Royal Horticultural Society of London, England. Color designations, color descriptions, and other phenotypical descriptions may deviate from the stated values and descriptions depending upon variation in environmental, seasonal, climatic and cultural conditions.

CHARACTERISTICS OF THE NEW VARIETY

Table 1 provides information on the plant and fruit characteristics of the new blackberry cultivar 'Driscoll Eureka' compared with characteristics of the unpatented blackberry cultivars 'Olallie' and 'Chester'. Both 'Olallie' and 'Chester' are currently important cultivars for fresh market shipping, and thus are comparable to the proposed use of the new invention, 'Driscoll Eureka'. Observations of 'Driscoll Eureka' 'Olallie' and 'Chester' were taken in side-by-side comparison in 2001 and in 2002.

Fruit of the new cultivar is particularly characterized and distinguished from other cultivars by its improved flavor and shipping characteristics. Drupelets of 'Driscoll Eureka' fruit show less postharvest color reversion compared to 'Olallie', the most comparable cultivar fruiting at the same time of the season.

'Driscoll Eureka' is moderately productive and produces most of its crop in the early part of the harvest season. Canes of 'Driscoll Eureka' are vigorous, thorny and have buds with a low chill requirement. The average plant height is about 279 cm and the average plant spread is about 169 cm.

The style pigmentation color is 143B, the average number of styles per flower is about 112, the anther pigmentation color is 155A, and the average number of anthers per flower is about 121. The number of petals per flower is five. The color of the sepal pigmentation is 144A. The color of the seeds of 'Driscoll Eureka' is 152C and the average seed weight is 2.9 mg.

'Driscoll Eureka' is distinguished from its pollen parent, BY45.1, by having better flavor.

'Driscoll Eureka' is distinguished from its seed parent, 'Zorro', by being earlier and having better flavored fruit.

TABLE 1

PLANT CHARACTERISTICS OF 'DRISCOLL EUREKA'

| | Eureka | Driscoll Chester | Olallie |
|---|---|---|---|
| GENERAL | | | |
| Vigor | moderate-high | high | moderate-high |
| Growth habit | semi-erect | semi-erect | spreading |
| Productivity | moderate | high | high |
| Self-fruitfulness | self-fruitful | self-fruitful | self-fruitful |
| Time of bud burst | early | late | early |
| CANES | | | |
| Primocanes | | | |
| Young shoot pigmentation | weak | medium | weak |
| glucosity (waxy bloom) | absent or weak | medium | weak |
| cane cross section (from mid cane of primocane) | angular to grooved | angular to grooved | rounded to angular |
| dormant cane color | brown to purple | purple brown | brown to purple brown |
| Spines | present | absent | present |
| pigmentation | purple | — | purple |
| color | 184A | — | 187A |
| density on young shoots | medium | — | medium |

TABLE 1-continued

PLANT CHARACTERISTICS OF 'DRISCOLL EUREKA'

| | Eureka | Driscoll Chester | Olallie |
|---|---|---|---|
| attitude of tip | downward | — | downward to horizontal |
| size | medium | — | medium |
| size: Length (base to tip)(mm) | 3.4 | — | 3.0 |
| texture | smooth | — | heavy |
| presence and distribution on petioles | present irregularly distributed | — | present irregularly distributed |
| Pubescence on canes | present | present | present |
| LEAVES | | | |
| Relief between veins | medium | weak | medium |
| Number of leaflets | usually 5 | usually 5 | sometimes 3 sometimes 5 |
| Glossiness | medium | medium | medium |
| Leaf cross section | concave | concave to flat | concave |
| Terminal leaflet | | | |
| length (cm) | 8.6 | 10.7 | 9.1 |
| width (cm) | 7.2 | 8.3 | 7.9 |
| shape | ovate | ovate | ovate |
| tip | acuminate | acuminate | acuminate |
| base | cordate | cordate | cordate |
| margin | doubly serrate | doubly serrate | doubly serrate |
| Lateral leaflet | | | |
| length (cm) | 7.9 | 9.2 | 8.4 |
| width (cm) | 5.5 | 6.4 | 6.3 |
| shape | ovate | ovate | ovate |
| tip | acuminate | acuminate | acuminate |
| base | rounded to cordate | rounded | rounded |
| margin | doubly serrated | doubly serrated | doubly serrated |
| rachis length (between terminal leaflet and adjacent lateral leaflets) (cm) | 3.0 | 3.0 | 2.5 |
| overlapping of lateral leaflets | overlapping | overlapping | overlapping |
| Petiole | | | |
| length (cm) | 6.2 | 5.9 | 3.9 |
| pigmentation of upper surface | red purple/ maroon 183A | red purple/ maroon | green to slightly pink |
| pigmentation of underside | yellow green 146A | yellow green | yellow green |
| Stipule orientation | clasping | erect | clasping to erect |
| Color | | | |
| face | 147A | 146A | 146A |
| underside | 147B | 146A | 146A |
| FLOWERS | | | |
| Flowering period (time of beginning of flowering) | very early | very late | early |
| Flower size | medium | medium | medium |
| Flower diameter (cm) | 4.8 | 4.3 | 4.3 |
| Flower number (at 3rd node from tip of lateral mean and range) | 5.0 | 9.5 | 4.2 |
| Petal | | | |
| length (cm) | 2.3 | 2.0 | 2.0 |
| width (cm) | 1.7 | 1.4 | 1.3 |
| Pedicel | | | |
| coloration | absent | weak | very weak |
| length (cm) | 2.4 | 1.8 | — |

TABLE 1-continued

PLANT CHARACTERISTICS OF 'DRISCOLL EUREKA'

| | Eureka | Driscoll Chester | Olallie |
|---|---|---|---|
| FRUIT | | | |
| Fruit harvest season | early | late | early |
| Color | black | black | black |
| immature | 187A | 187A | 187B |
| maturing | 202A | 202A | 202A |
| mature fruit | 202A | 202A | 202A |
| Glossiness | strong | medium | medium |
| Shape | ovate | round to ovate | narrow ovate |
| Dimensions | | | |
| fruit size | medium | small | medium large |
| length (cm) | 2.3 | 2.1 | 2.9 |
| width (cm) | 2.0 | 2.0 | 1.7 |
| Weight (g/fruit) | 4.2 | 3.9 | 5.3 |
| Soluble solids (%) | 11.9 | 9.6 | 10.4 |
| Titratable acidity (% as citric acid) (ml. of added .1 N NaOH to pH 8.1) | 1.34 | 1.84 | 2.06 |

TABLE 1-continued

PLANT CHARACTERISTICS OF 'DRISCOLL EUREKA'

| | Eureka | Driscoll Chester | Olallie |
|---|---|---|---|
| Number of druplets per fruit | 61 | 46 | 86 |
| Firmness | firm | firm | soft |

NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531-5). Using a variety of oligonucleotide primers, alone or in combination, RAPD analysis of Driscoll Eureka, Chester, and Olallie yielded DNA fragment patterns that uniquely distinguish each of these genetically distinct genotypes.

We claim:

1. A new and distinctive cultivar of blackberry plant, substantially as shown and described.

* * * * *